(12) United States Patent
Goolishian (10) Patent No.: US 9,827,049 B2
(45) Date of Patent: Nov. 28, 2017

(54) TEMPORARY TATTOOS FOR INDELIBLE ENDORSEMENT

(71) Applicant: DENOVO LABS, LLC, Sandwich, MA (US)

(72) Inventor: Wade T. Goolishian, Sandwich, MA (US)

(73) Assignee: DE NOVO LABS, LLC, Sandwich, MA (US)

( * ) Notice: Subject to any disclaimer, the term of this patent is extended or adjusted under 35 U.S.C. 154(b) by 405 days.

(21) Appl. No.: 14/133,144

(22) Filed: Dec. 18, 2013

(65) Prior Publication Data

US 2014/0107662 A1    Apr. 17, 2014

Related U.S. Application Data

(62) Division of application No. 13/198,296, filed on Aug. 4, 2011, now Pat. No. 8,636,708.

(60) Provisional application No. 61/373,041, filed on Aug. 12, 2010.

(51) Int. Cl.

| | |
|---|---|
| *A61M 35/00* | (2006.01) |
| *B32B 3/10* | (2006.01) |
| *A61B 19/00* | (2006.01) |
| *B44C 1/175* | (2006.01) |
| *G09F 3/02* | (2006.01) |
| *G09F 21/02* | (2006.01) |
| *A61B 90/90* | (2016.01) |
| *A61B 90/00* | (2016.01) |
| *A61B 90/94* | (2016.01) |

(52) U.S. Cl.
CPC .............. *A61B 19/44* (2013.01); *A61B 90/39* (2016.02); *A61B 90/90* (2016.02); *A61B 90/94* (2016.02); *B44C 1/1758* (2013.01); *G09F 3/02* (2013.01); *G09F 21/02* (2013.01); *A61B 2090/08021* (2016.02); *Y10T 428/1471* (2015.01); *Y10T 428/1486* (2015.01); *Y10T 428/24802* (2015.01)

(58) Field of Classification Search
CPC .................................................... B44C 1/1754
USPC .................................................. 424/9.8–9.81
See application file for complete search history.

(56) References Cited

U.S. PATENT DOCUMENTS

| | | | |
|---|---|---|---|
| 1,627,407 A | 5/1927 | Reese | 428/207 |
| 2,578,150 A | 12/1951 | Rathke | 426/132 |
| 2,941,916 A | 6/1960 | Akkeron | 156/240 |
| 4,175,151 A | 11/1979 | Eppich et al. | 428/202 |
| 4,362,157 A | 12/1982 | Keeth | 128/215 |
| 4,522,864 A | 6/1985 | Humason et al. | 428/201 |
| 4,594,276 A | 6/1986 | Relyea | 428/42.1 |
| 4,947,867 A * | 8/1990 | Keeton | A61F 13/00059 128/846 |

(Continued)

OTHER PUBLICATIONS

3M Health Care. (1999) "3M Tegaderm and 3M Tegaderm HP Transparent Dressings."

*Primary Examiner* — Paula L. Craig
(74) *Attorney, Agent, or Firm* — Medlen & Carroll, LLP (57) ABSTRACT

Embodiments of the present invention provide a temporary tattoo, appliqué or decal and a method of using the tattoo on a patient to identify on that patient a selected operative site, wherein said operation is identified by name on said decal and wherein the accuracy of site selection may be endorsed by the patient and the responsible operator directly on the selected site in such a manner that the endorsement indicia remain legible after the decal is eradicated.

19 Claims, 3 Drawing Sheets

(56) References Cited

U.S. PATENT DOCUMENTS

| | | | |
|---|---|---|---|
| 4,957,124 A * | 9/1990 | Mooney | A45D 40/00 132/200 |
| 4,985,019 A * | 1/1991 | Michelson | A61B 6/12 128/DIG. 26 |
| 5,099,857 A | 3/1992 | Baldo et al. | 128/743 |
| 5,496,304 A | 3/1996 | Chasan | 606/1 |
| 5,816,269 A | 10/1998 | Mohammed | 132/319 |
| 5,836,998 A | 11/1998 | Mueller et al. | 607/95 |
| 5,942,065 A | 8/1999 | Biggs et al. | 156/90 |
| 5,958,560 A | 9/1999 | Ewan | 428/201 |
| 6,053,178 A * | 4/2000 | Todd | B41M 1/26 132/206 |
| 6,074,721 A | 6/2000 | Moore et al. | 428/42.1 |
| 6,207,874 B1 | 3/2001 | Felton et al. | 602/42 |
| 6,264,786 B1 | 7/2001 | Moore et al. | 156/289 |
| 6,286,682 B1 | 9/2001 | D'Arbelles | 206/570 |
| 6,296,858 B1 * | 10/2001 | Agostini | A61K 8/04 424/401 |
| 6,299,967 B1 | 10/2001 | Collins et al. | 428/32.12 |
| 6,579,252 B2 | 6/2003 | Lloyd et al. | 602/60 |
| 6,685,682 B1 | 2/2004 | Heinecke et al. | 604/307 |
| 6,824,839 B1 | 11/2004 | Popat et al. | 428/32.12 |
| 6,964,229 B1 | 11/2005 | Zimmerman | 101/483 |
| 6,972,022 B1 * | 12/2005 | Griffin | 604/112 |
| 7,389,928 B2 | 6/2008 | Lubow | 235/462.01 |
| 7,402,223 B2 | 7/2008 | Marks, III et al. | 235/462.01 |
| 7,674,345 B2 | 3/2010 | Graham et al. | 156/252 |
| 8,636,708 B2 * | 1/2014 | Goolishian | B44C 1/1758 428/42.1 |
| 2002/0040202 A1 * | 4/2002 | Levin | A61F 13/0203 602/43 |
| 2002/0041851 A1 | 4/2002 | Kamimoto | 424/9.8 |
| 2002/0114764 A1 | 8/2002 | Berryman et al. | 424/401 |
| 2003/0152733 A1 | 8/2003 | Wittmeyer | 428/40.1 |
| 2003/0180341 A1 * | 9/2003 | Gooch | A61L 26/0061 424/401 |
| 2003/0187458 A1 | 10/2003 | Carlson | 606/116 |
| 2003/0215593 A1 | 11/2003 | Morgan et al. | 426/383 |
| 2004/0033325 A1 | 2/2004 | Shea et al. | 442/149 |
| 2004/0056478 A1 | 3/2004 | Bruce | 128/869 |
| 2004/0153031 A1 | 8/2004 | Van Kaauwen | 604/116 |
| 2005/0148935 A1 | 7/2005 | Dimitrova et al. | 604/116 |
| 2005/0232958 A1 * | 10/2005 | Lee | A61K 8/02 424/401 |
| 2005/0234322 A1 | 10/2005 | Lober | 101/327 |
| 2005/0249672 A1 | 11/2005 | Bolbot | 424/400 |
| 2005/0255300 A1 * | 11/2005 | Funke | B44C 1/1758 428/195.1 |
| 2006/0127428 A1 | 6/2006 | Miskanic | 424/401 |
| 2006/0138211 A1 | 6/2006 | Lubow | 235/462.01 |
| 2006/0154031 A1 | 7/2006 | Tomlinson | 428/195.1 |
| 2006/0266368 A1 | 11/2006 | Heintz | 128/846 |
| 2008/0132907 A1 * | 6/2008 | Mueller | A61B 17/0401 606/116 |
| 2009/0091120 A1 | 4/2009 | Welsh | 283/74 |
| 2009/0120565 A1 | 5/2009 | Marshall | 428/40.1 |
| 2009/0242106 A1 | 10/2009 | Kupferman | 428/40.1 |
| 2010/0113860 A1 | 5/2010 | Traboulsi et al. | 128/897 |
| 2011/0117174 A1 * | 5/2011 | Kergosien | A61K 8/731 424/443 |
| 2012/0302863 A1 | 11/2012 | O'Neill | 600/407 |

\* cited by examiner

TEMPORARY TATTOOS FOR INDELIBLE ENDORSEMENT

STATEMENT OF RELATED APPLICATIONS

This application for patent under 35 U.S.C. §111(a) is a divisional of U.S. patent application Ser. No. 13/198,296 filed Aug. 4, 2011 and claims priority to Provisional Application(s) Ser. No. 61/373,041 filed on Aug. 12, 2010 under 35 U.S.C. §111(b).

FIELD OF INVENTION

The present invention relates to a temporary tattoo, and to a method of using said temporary tattoo, appliqué or decal on a patient to label, directly on a skin surface of that patient, information about the patient including, in particular, a selected operative site, wherein the decal comprises a means of endorsing the procedure and the accuracy of site selection by both the patient and the party responsible for performing the procedure. Endorsement directly on the selected site is effected in such a manner that the endorsement indicia (and any others) remain legible on the patient's skin and within the operative field, and the role of each endorser remains identifiable, after the temporary tattoo is removed.

BACKGROUND

A huge variety of products, referred to generally as decals, and consisting essentially of a film-like material optionally bearing printed information and having an adhesive layer on one surface has been used to permanently or semipermanently identify objects or particular locations on objects. The medical arts have employed temporary decals, often referred to as temporary tattoos, as an improvement over making marks on a patient with a marking pen or adhesive tape for identifying the correct (or, perhaps, incorrect) site for a surgical or other invasive procedure or for the administration of a drug, high-energy radiation, etc. Such tattoos have also been employed to convey information about previous surgeries, pre-existing conditions, medications, etc. (e.g., U.S. Pat. No. 6,286,682, incorporated herein by reference in its entirety). Marks applied with marking pens can convey only limited information, often with poor legibility. In addition, such marks may be placed outside of the operative field, where surgical drapes etc. obscure the view of the mark. Adhesive tapes, even if they adhere well to skin, tend to interfere with the intended operative procedure because of their thickness and porosity, both of which tend to promote retention of bacteria. The film used in temporary tattoos, by contrast, is typically very thin. Its stability prior to use comes about because it is releasably secured at the surface opposite its adhesive surface to a water-permeable, relatively stiff, paper-like backing. The film's adhesive layer, in turn, is covered with a readily removable sheet of plastic material such as polycarbonate to protect the adhesive. The film serves as a substrate for inks applied by lithography (preferably, 4-color offset lithography) or "silk-screening," or by ejecting ink onto the film from an inkjet printer head. The inks form images (letters, symbols, other patterns) on the film. Typically, the film, with backing sheet in place, is applied to the skin of a subject and then released from the backing by soaking the backing with water. Advantageously, the applied inks do not "bleed" substantially into one another or into adjoining layers before or after the tattoo is applied. Therefore, imprinted images remain sharply defined. Also, the inks do not diffuse from the film into living skin tissue. Moreover, the film and its applied inks and adhesive, although preferably moisture-resistant and mechanically resistant, are removable by innocuous means (e.g., soap and water).

Tattoos of this sort have provided a means of durably (but not permanently) labeling a body part with readable information that advises personnel administering care to the subject. The label conveys information about the medical procedure to be conducted in the proximity of the labeled site, and can carry additional information such as the name of the subject, the caregiver, etc. U.S. Pat. No. 6,579,252 to Lloyd et al., describes temporary tattoos whose printed indicia are intended to mark sites where a medical procedure is prohibited. U.S. Pat. No. 7,389,928 discloses a "medical system" of which a temporary tattoo is an element. The information on the tattoo is "bar-coded." U.S. Pat. Nos. 6,579,252 and 7,389,928 are incorporated herein by reference in their entirety.

These and other examples in the prior art share the property of conveying relevant medical information by printing (or writing) the information on the tattoo's film element either before or after the film is applied to the patient's skin. The advantages of retaining a patient's "medical chart" directly on the patient are clear. However, inasmuch as invasive medical procedures are generally conducted in a sterile field that is typically provided by applying liquids that can dissolve or eradicate the film, information carried on the tattoo is also susceptible to eradication. Information lost during preparation of the field could include the medical procedure to be conducted, the site at which the procedure is to be conducted, and, most importantly, evidence that the accuracy of such information has been attested to or endorsed by the recipient of the treatment and/or by the responsible caregiver. What is needed is a means for retaining evidence of the attestation or endorsement in the operative field after the tattoo is eradicated, without compromising sterility or otherwise interfering with the procedure to be conducted, and without permanently tattooing the skin.

SUMMARY OF THE INVENTION

Embodiments of the present invention have an objective of retaining on a skin surface of a patient, at or near a site of an intended medical procedure to be conducted on the patient by a caregiver, relevant information about the procedure, including but not limited to endorsements as to the correctness of the site of the intended procedure and, where symmetries create ambiguity, the side of the body on which the procedure is to be performed, wherein the endorsements are made by the patient or the caregiver. Embodiments of the invention have a further objective of retaining at least the endorsement information throughout preparation and sterilization of the site, and during exposure to blood, other body fluids, saline rinses, etc. during the procedure. In some embodiments, additional information may be retained directly on the skin by marking the information, preferably in an encoded form.

In preferred embodiments, the present invention provides a temporary tattoo comprising a film, wherein the film comprises a first surface coated with a skin-adherent adhesive, a second surface disposed opposite said first surface, and a water-resistant material therebetween, wherein said water-resistant material defines at least one film-void that passes through said material and said surfaces. Preferably, the tattoo further comprises:

a. a water-permeable backing sheet;
b. a water-soluble slip-layer disposed between said backing sheet and said second surface of said film,
c. printed matter on said first or second surface of said film, and
d. a removable protective sheet covering said adhesive-coated first surface of said film.

In one embodiment, said slip-layer comprises an antimicrobial substance. In another embodiment, said film comprises an antimicrobial substance. In another embodiment, said water-permeable backing sheet comprises an antimicrobial substance.

In some embodiments, the backing sheet is transparent. In some embodiments, the protective sheet is transparent. In some embodiments, the printed matter comprises indicia that identify a medical procedure. In some embodiments, the printed matter labels a film-void. In one embodiment, the film-void is configured to confer directionality on the film and thus on the film-voids in the film.

In one embodiment, the invention provides a method of labeling a site of an intended medical procedure on a patient, the method comprising:
  a. providing a temporary tattoo, said tattoo comprising a film, said film comprising a first surface coated with a skin-adherent adhesive, a second surface disposed opposite said first surface and a water-resistant material therebetween, wherein:
    i) said water-resistant material defines at least one film-void that passes through said material and said surfaces,
    ii) said first or second surface of said film supports printed matter,
    iii) said printed matter comprises indicia comprising said labeling, and
  b. positioning and adhering said film and said indicia to a skin surface of said patient to create a positioned film on said patient.

In a preferred embodiment, the method comprises an endorsement of the positioning and labeling of said positioned film by the patient, wherein the patient indelibly marks the skin surface through a first film-void. In another preferred embodiment, the method comprises an endorsement of the positioning and labeling of said positioned film by the patient's caregiver, wherein the caregiver indelibly marks the skin surface through a second film-void.

In one embodiment, the invention provides a system for retaining an indicium at a pre-determined site on a skin surface of a patient, said system comprising:
  a. a temporary tattoo comprising at least one film-void;
  b. a means for indelibly marking said skin surface through said film-void, and
  c. a means for adhering said temporary tattoo to said skin surface such that at least a portion of said skin surface is contactable with said marking means.

In another embodiment, the invention provides a kit for labeling a site of an intended medical procedure on a patient comprising:
  a. a temporary tattoo, said tattoo comprising a film, said film comprising a first surface coated with a skin-adherent adhesive, a second surface disposed opposite said first surface, and a water-resistant material therebetween, wherein:
    i) said water-resistant material defines at least one film-void that passes through said material and said surfaces,
    ii) said first or second surface of said film supports printed matter,
    iii) said printed matter comprises indicia comprising said labeling, and
  b. a marking means for indelibly marking skin.

In one embodiment, the tattoo in the kit further comprises
  a. a water-permeable backing sheet having a first backing sheet surface facing a water-soluble slip-layer disposed between said backing sheet and said second surface of said film and a second backing sheet surface disposed opposite said first backing sheet surface;
  b. printed matter on said first or second surface of said film, and
  c. a removable protective sheet having a first protective sheet surface facing said adhesive-coated first surface of said film, and a second protective sheet surface disposed opposite said first protective sheet surface.

In one embodiment, the kit further comprises instructions for use of the tattoo. In one embodiment, the instructions are printed on the first or second backing sheet surfaces. In one embodiment, the instructions are printed on the first or second protective sheet surfaces. In one embodiment, the instructions are printed on a separate sheet. In one embodiment, a patient consent form is incorporated into said instructions.

In another embodiment, the invention provides a method of indelibly marking a patient's vital signs, medical history, or precautions for treatment on a skin surface of said patient, the method comprising:
  a. providing a temporary tattoo, said tattoo comprising a film, said film comprising a first surface coated with a skin-adherent adhesive, a second surface disposed opposite said first surface and a water-resistant material therebetween, wherein:
    i) said water-resistant material defines at least one film-void that passes through said material and said surfaces to create a site for said marking,
    ii) said first or second surface of said film supports printed matter, and
    iii) said printed matter comprises an indicium that labels said film-void;
  b. adhering said film and said indicia to said skin surface of said patient, and
  c. indelibly marking said vital signs, medical history, or precautions for treatment on said skin surface at said film-void.

Definitions

To facilitate understanding of the descriptions herein of embodiments of the invention, a number of terms (set off in quotation marks in this Definitions section) are defined below. Terms defined herein (unless otherwise specified) have meanings as commonly understood by a person of ordinary skill in the areas relevant to the present invention. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, but their usage does not delimit the invention, except as outlined in the claims.

The phrase "chosen from A, B, and C" as used herein, means selecting one or more of A, B, C.

As used herein, absent an express indication to the contrary, the term "or" when used in the expression "A or B," where A and B may refer to a composition, object, disease, product, etc., means one or the other ("exclusive OR"), or both ("inclusive OR"). As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities in the specification and claims are to be understood as being modified in all instances by the term "about." Accordingly, unless indicated to the contrary, the numerical parameters in the specification and claims are approximations that may vary depending upon the desired properties sought to be obtained in a particular embodiment of the present invention. At the very least, and without limiting the application of the doctrine of equivalents to the scope of the claims, each numerical parameter should be construed in light of the number of reported significant digits and by applying ordinary rounding techniques. Any numerical value, however, inherently contains deviations that necessarily result from the errors found in the numerical value's testing measurements. In general herein, deviations of as much as 25% are expected.

The term "not" when preceding, and made in reference to, any particularly named entity or phenomenon means that only the particularly named entity or phenomenon is excluded.

The term "altering" and grammatical equivalents as used herein in reference to any entity and/or phenomenon refers to an increase and/or decrease in the quantity of the entity in a given space and/or the intensity, force, energy or power of the phenomenon, regardless of whether determined objectively, and/or subjectively.

The terms "increase," "elevate," "raise," and grammatical equivalents when used in reference to the quantity of an entity and/or the intensity, force, energy or power of a phenomenon in a first sample relative to a second sample, mean that the quantity of the entity and/or the intensity, force, energy or power of the phenomenon in the first sample is higher than in the second sample by any amount that is statistically significant using any art-accepted statistical method of analysis. In one embodiment, the increase may be determined subjectively, for example when a patient refers to his subjective perception of disease symptoms, such as pain, clarity of vision, etc. In another embodiment, the quantity of the substance and/or phenomenon in the first sample or subject is at least 10% greater than the quantity of the same substance and/or phenomenon in a second sample or subject. In another embodiment, the quantity of the substance and/or phenomenon in the first sample or subject is at least 25% greater than the quantity of the same substance and/or phenomenon in a second sample or subject. In yet another embodiment, the quantity of the substance and/or phenomenon in the first sample or subject is at least 50% greater than the quantity of the same substance and/or phenomenon in a second sample or subject. In a further embodiment, the quantity of the substance and/or phenomenon in the first sample or subject is at least 75% greater than the quantity of the same substance and/or phenomenon in a second sample or subject. In yet another embodiment, the quantity of the substance and/or phenomenon in the first sample or subject is at least 90% greater than the quantity of the same substance and/or phenomenon in a second sample or subject. Alternatively, a difference may be expressed as an "n-fold" difference.

The terms "reduce," "inhibit," "diminish," "suppress," "decrease," and grammatical equivalents when used in reference to the quantity of an entity and/or the intensity, force, energy or power of a phenomenon in a first sample or subject relative to a second sample or subject, mean that the quantity of an entity and/or the intensity, force, energy or power of a phenomenon in the first sample or subject is lower than in the second sample or subject by any amount that is statistically significant using any art-accepted statistical method of analysis. In one embodiment, the reduction may be determined subjectively, for example when a patient refers to their subjective perception of disease symptoms, such as pain, weakness, etc. In another embodiment, the quantity of quantity of an entity and/or the intensity, force, energy or power of a phenomenon the first sample or subject is at least 10% lower than the quantity of the same substance and/or phenomenon in a second sample or subject. In another embodiment, the quantity of the substance and/or phenomenon in the first sample or subject is at least 25% lower than the quantity of the same substance and/or phenomenon in a second sample or subject. In yet another embodiment, the quantity of the substance and/or phenomenon in the first sample or subject is at least 50% lower than the quantity of the same substance and/or phenomenon in a second sample or subject. In a further embodiment, the quantity of the substance and/or phenomenon in the first sample or subject is at least 75% lower than the quantity of the same substance and/or phenomenon in a second sample or subject. In yet another embodiment, the quantity of the substance and/or phenomenon in the first sample or subject is at least 90% lower than the quantity of the same substance and/or phenomenon in a second sample or subject. Alternatively, a difference may be expressed as an "n-fold" difference.

As used herein, terms such as "retaining," "maintaining," and "preserving" are not intended to convey any notion of permanence. For example, a mark placed on the skin of a subject is "retained" in embodiments of the subject invention if it remains sufficiently legible to contribute to the objective of the embodiment.

"Patient" and "subject" are used interchangeably herein, and include animals as well as humans.

As used herein, a "skin surface" is any area of skin covering a subject, whether human or animal, that is observable to the naked eye. The term "skin" relates to the generally pliable but resilient outer covering of the subject.

A "medical procedure," as used herein, encompasses any procedure performed on a subject, including without limitation surgery, amputation, administration of drugs or other agents such as high-energy radiation, diagnostic and therapeutic procedures, and dental procedures.

As used herein, the term "intended" describes a pre-determined site or procedure. Although such pre-determination will typically be based upon diagnosis, planning and consultation, "intended" herein means only "not unintended." A "site" refers to the location on or in a patient where a medical or surgical procedure is to be conducted. It is not intended that the term be limited to the location on the body where the procedure begins, such as a site of injection or incision. Thus, a tissue, organ, body part or body region that is the object of the procedure may be the "site" of interest. Preferably, however, embodiments of the invention identify the site of interest by being placed at or near the site. A site may be identified in part by reference to an anatomic symmetry of the body (e.g., the right or left side, the inner aspect or outer aspect of an extremity, etc.). It is not intended, however, to exclude from the definition of "site" a location that is not defined by a symmetry.

A "caregiver" or "provider of care" herein refers to a person or persons responsible for a procedure on a subject, whether or not said caregiver physically conducts all or any part of such procedure.

An "endorsement" refers herein to physical evidence of approval by the patient or caregiver of the intended event or procedure and its site. Embodiments of the invention have a further objective of retaining the endorsement information throughout a preparation and sterilization of the site and, preferably, throughout exposures to blood, other body fluids, saline rinses, etc.

Other information, including but not limited to information about the intended procedure, the condition of the patient including but not limited to the patient's vital signs (body temperature, pulse rate, blood pressure, respiratory rate, etc.), medical history, treatment precautions, etc. may be retained in the same manner as endorsements, preferably in encoded form for compactness. The key to any such code is advantageously included in instructions provided with the devices according to the invention.

An "antimicrobial" or "antimicrobial substance" as used herein is any substance that is tolerated by a subject when the subject's skin is exposed to the substance and that inhibits the growth of bacterial populations on the subject's skin by direct ("cidal") or indirect ("static") action. Non-limiting examples include aminoglycosides, cephalosporins, carbapenems, quinolones, macrolides, penicillins, tetracyclines, clindamycin, vancomycin and metronidazole.

A "temporary tattoo" refers generally herein to a device that bears printed or written information or decoration, which device can be transferred to, and legibly retained upon, the skin of a human or an animal. Such devices are distinguished from true tattoos in that the materials (e.g., ink, dye, pigment) used to print designs or printed matter (i.e., letters and other symbols not applied by hand-writing) are not substantially absorbed by living cells of the skin or trapped in the interstitium thereof. Instead, these materials are retained on a generally thin, film-like structure that sticks to the skin, where the term "film" refers simply to a thin coating or layer on a surface, which surface, however, need not be a component of the film, structurally or functionally. In preferred embodiments, the film is transparent. The term "transparent" is used herein to describe any element of an embodiment of the invention through which printed matter in accordance with any embodiment is legible. The terms "appliqué" and "decal" are often used to describe temporary tattoos, principally because they are applied in the same way. That is, prior to application, the film adheres to a (usually) water-permeable substrate or "backing sheet" through an interposed layer of a water-soluble material. When water permeates the backing sheet, the water-soluble layer (or "slip-layer") dissolves. Consequently, the film "slips away" from the backing and adheres, instead, to the skin. It is not intended that the mechanism of skin-adherence limit embodiments of the invention. Generally, an adhesive compound coated on the film surface opposite the surface that faces the slip layerslip layer. However, any means of bonding the film to the skin is within the scope of embodiments of the invention, provided only that the bond is compatible with the health of the subject and is releasable by innocuous means.

In some embodiments, the methods of the invention are conveniently practiced from kits. A "kit" herein relates to any component or set of components that contribute to performing methods in accordance with embodiments of the invention. Preferably, such kits improve performance through packaging that enhances shipping and delivery, identification, selection, storage, use and instructions for use.

Because the patient is a user of embodiments of the invention, the instructions may include the language necessary to obtain the consent of the patient. Some of this language is typically set forth in a so-called "patient consent form," the content and design of which vary, but the intent of which is to inform the patient as to the details of the procedure to which he is submitting, including risks, benefits, course of recovery and prognosis.

Instructions may be supplied herein as printed matter directly on embodiments of the invention. Where supplied apart from the tattoo itself, the instructions are said to be on a "separate sheet."

One positions the film at a pre-determined site on the skin by pressing the tattoo (film, slip-layer and backing sheet) onto the site while soaking the backing sheet to create a positioned or "located" film, which may be oriented in a pre-determined orientation at the site. A "water-permeable" material is any material through which water or other aqueous solution can pass. The force that moves water through the material (e.g., diffusion, capillary flow, osmotic pressure) is not intended to be limiting. A "water-soluble" material dissolves or enters into a colloidal suspension with water and aqueous solutions, but the terms "water-permeable" and "water-soluble" are not intended to be mutually exclusive herein. A "water-resistant" material herein relates to materials that tend to be insoluble in water and also to materials that tend to be impermeable to water.

The film supports inks, dyes and pigments that are applied to it to form designs, letters and other symbols. The term "support," as used herein, relates to a stabilizing property. For example, the film "supports" an ink because it is capable of accepting and retaining ink on its surface under conditions that obtain when embodiments of the invention are in use.

The film, with the printed matter it supports, "covers" the skin such that skin beneath the film cannot be contacted directly unless the film is rubbed off. In preferred embodiments of the present invention, this constraint is avoided by placing voids ("film-voids") in the film. Thus, the film has, in addition to outer edges, "inner" edges, that is, film edges that at least partially surround a film void and define the void. It is to be understood that a "film-void" refers herein to a space that communicates directly with the subject's skin and also with the external environment when the film is in use on a subject's skin in accordance with embodiments of the invention. The positioned film covers the skin surface except at the film-void. At the film-void, a mark may be applied directly to the skin surface. The minimum size of a film-void is not intended to be a limitation herein. It is determined only by the necessary size of the mark to be made and the means of inscribing the mark.

As used herein, the term "mark," is a line, dot, impression, stain or discoloration visible by eye or instrument. Herein, "marks" generally convey specific information; that is, they convey a meaning shared in common by observers of the mark or marks. Such marks are therefore "indicia," i.e., elements that comprise a code or an encrypted description of an object. Thus, indicia and their inscription on the tattoo or on the skin of the patient (at a "marking site") are elements of "labeling." Indicia may include, but are not limited to, letters and other conventional symbols. They may be carried on the film, the backing or elsewhere in embodiments of the invention, and their individual meanings may lie in their relative positions therein. Endorsement marks and other indicia to be inscribed directly on the skin are preferably "indelible." That is, they preferably remain legible throughout a preparation and sterilization of a site to which a tattoo embodiment of the invention has been applied and, preferably, throughout exposures to blood, other body fluids, saline rinses, etc., that may obliterate the tattoo itself.

DETAILED DESCRIPTION OF THE INVENTION

The present invention relates to a temporary tattoo, appliqué or decal for placement on a patient to identify on that patient a selected operative site for surgery or for any medical procedure, wherein the accuracy of site selection may be endorsed by the patient undergoing the procedure, or by the caregiver responsible for conducting the procedure. In preferred embodiments, the endorsement may be applied directly on the identified site in such a manner that indicia comprising the endorsement remain legible and the role of each endorser remains identifiable after the temporary tattoo is removed.

Figure 1:
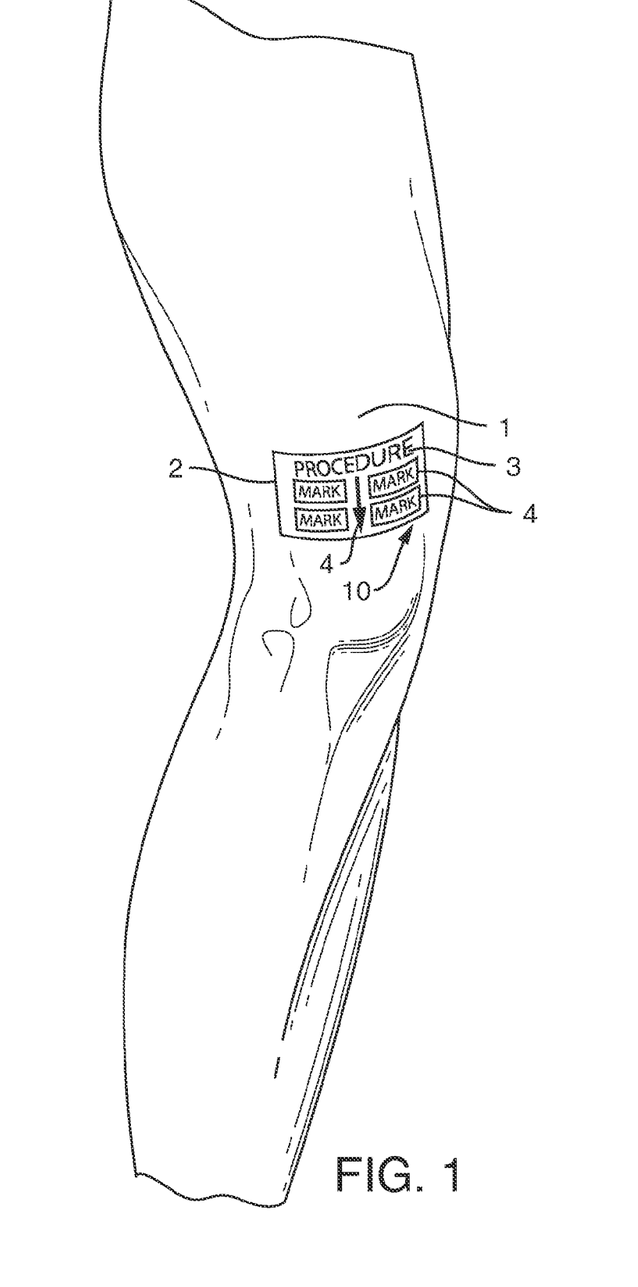
FIG. 1 illustrates an exemplary embodiment of the invention in use in a surgical procedure, as viewed by an observer looking down on the surgical site from above. The adhered decal, and marks inscribed on the underlying skin through film-voids in the decal (see inset), are shown.

In preferred embodiments, a tattoo comprising the features illustrated in FIG. 1 is used. FIG. 1 represents a decal in place on a skin surface 1. Backing sheet 20, slip layer 30 and protective sheet 70 (see FIG. 2) are not present. Design elements 2 and printed matter 3 are supported by water-resistant film 40, which has film-voids 4 that provide direct access to skin surface 1.

Figure 2:
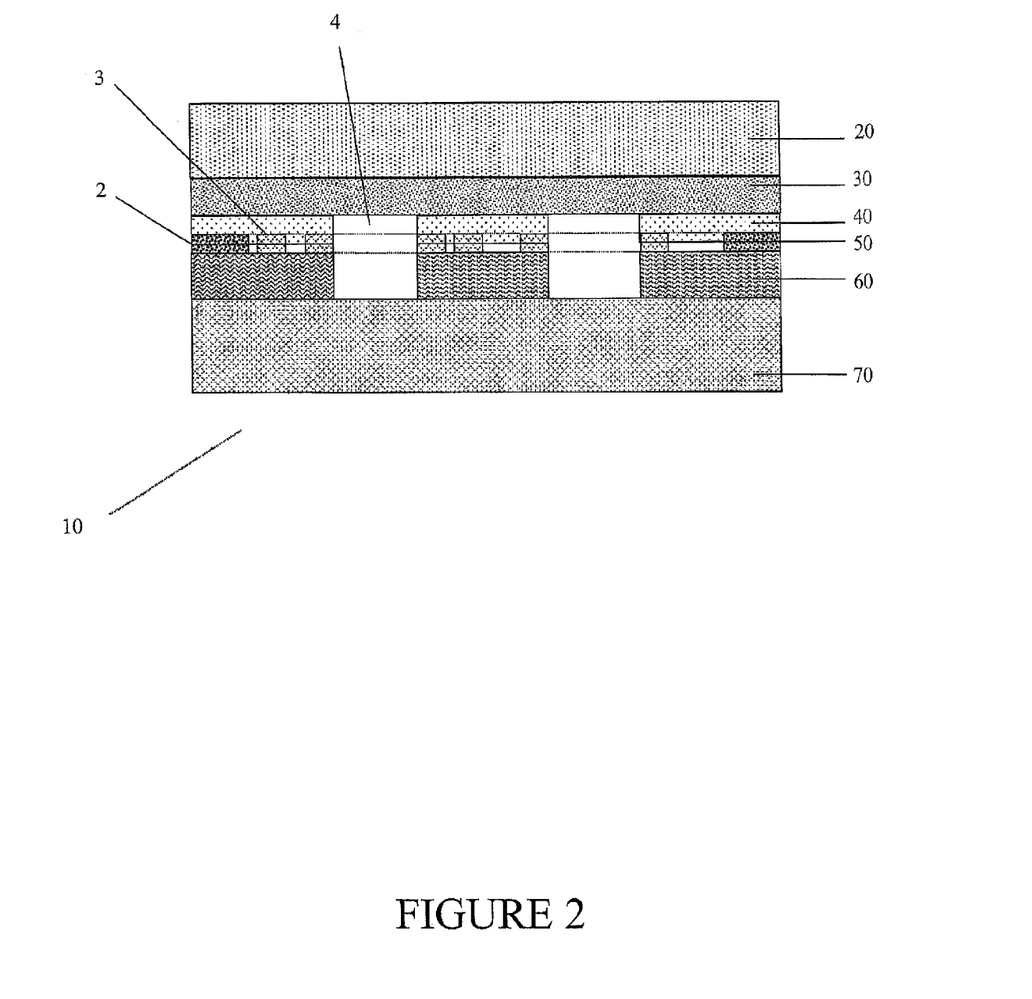
FIG. 2 is a cross-sectional representation of the layers (not to scale) that comprise the temporary tattoo before use.
Figure 3:
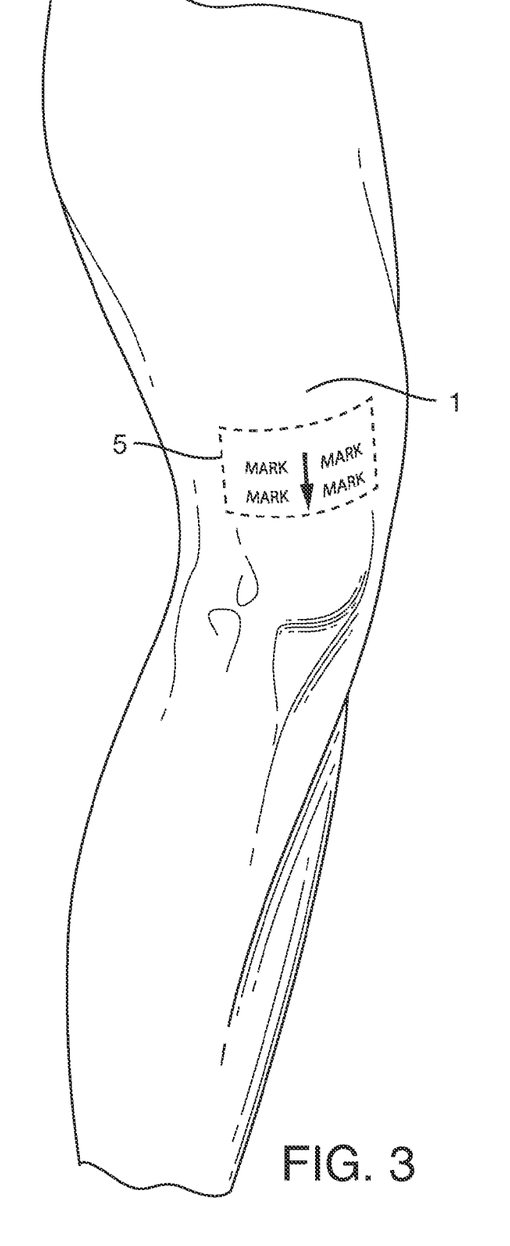
FIG. 3 is a view of the surgical site of FIG. 1 after the adhered decal has been washed away (magnified in inset).

Temporary tattoos for application to skin are well-known in the art. See, for example, U.S. Pat. No. 4,522,864 issued to Humason, which is incorporated herein by reference in its entirety. Humason teaches a decal, elements of which are illustrated in FIG. 2. A porous paper backing 20 supports a water-soluble slip layer 30 that is disposed between the paper backing 20 and a microscopically thin, flexible, extensible, water-resistant film 40. In a preferred embodiment, translucent, preferably multi-color design that occupies layer 50 in FIG. 2 is offset-printed on the surface of the water-resistant film 40 that opposes the surface of the film 40 that lies adjacent the slip layer 30. That is, film 40 is formed on slip-layer 30 and design elements 2 and printed matter 3 are applied later to occupy layer 50. A uniform layer 60 of transparent or translucent pressure sensitive adhesive covers the printed design elements 2 and printed matter 3. In alternative embodiments, design elements 2 and printed matter 3 may be applied to slip-layer 30 in such a manner that design elements 2 and printed matter 3 transfer from slip-layer 30 to film 40. In such embodiments, layer 50 is absent. In still other alternative embodiments, film 40 is formed in a separate step, design elements 2 and printed matter 3 are applied to film 40 later and then film 40 is applied to slip-layer 30. In this embodiment, one would imagine layer 50 as lying between slip-layer 30 and film 40 instead of between film 40 and adhesive layer 60. A protective sheet 70, preferably made of a plastic material such as polycarbonate, covers adhesive layer 60. Similar teachings are set forth in U.S. Pat. No. 1,627,407; U.S. Pat. No. 2,578,150; U.S. Pat. No. 2,941,916; U.S. Pat. No. 4,175,151; U.S. Pat. No. 4,594,276; U.S. Pat. No. 6,074,721; U.S. Pat. No. 6,264,786; U.S. Pat. No. 6,299,967; U.S. Pat. No. 6,824,839, and U.S. Pat. No. 7,402,223, all of which are incorporated by reference in their entirety.

Temporary tattoos are advantageous in clinical settings for several reasons. Identifying an intended site for a medical procedure by marking it directly clearly reduces the frequency of errors such as amputating or otherwise operating on an extremity that is contralateral to the extremity for which amputation or other procedure is intended. If the marking is done with an adherent tattoo instead of a handwritten mark applied directly to the skin, substantially more information can be conveyed, including the specific procedure to be undertaken, the identity of the patient and the responsible caregiver. Indeed, both patient and caregiver can endorse the tattoo as confirmation of the accuracy of its placement. Moreover, when a mark is made on a pre-printed tattoo, the meaning of the mark is enhanced, just as the meaning of a mark at a specific place on a pre-printed form is enhanced.

One of the advantages of temporary tattoos, namely, their removability, can also be a disadvantage, however. If the preparation and sterilization of the operative area washes off the tattoo, the patient's body thereafter conveys no information about the intended procedure. Embodiments of the present invention retain the "pre-printed form" advantage of tattoos, but preserve information entered on the form (and the interpretability of that information) even after the tattoo itself is no longer in place.

As shown in FIG. 1, the adhered decal provides printed information about the procedure to be undertaken, and the location of the decal on the patient's body surface distinguishes that location as the operative site. For example, if the decal is on the lower left abdomen, then the lower right abdomen, typically, as well as the upper abdomen, chest, neck, head, back, extremities, etc., are not operative sites.

The tattoo may convey a plethora of information about a procedure. Such information may include, in addition to the laterality and the type of procedure, patient features (male/female, pediatric/adult, precautions/pre-existing conditions) that may provide guidance or reveal discrepancies. When multiple structures are involved, such as fingers and toes, or multiple levels of entry or invasion, the tattoo may present indicia as printed matter (letters or other symbols), color code, diagrams, barcodes, etc. to indicate the correct structure or level.

It is not intended that embodiments of the invention be limited according to the part of the body on which the tattoo may be affixed. Since it is preferable that the tattoo, in some embodiments, be visible after the patient has been prepared and draped for the procedure, the tattoo may inform the caregiver or other observer that the actual operative site is not visible. Preferably, in such embodiments, the tattoo will provide information that directs the caregiver or other observer to the actual operative site. Similarly, for sites that may be too small or too rugose to accommodate the tattoo directly, the tattoo will provide suitable guidance. For example, a tattoo configured to be applied to the dorsum of the foot may also be configured to "map" (by an arrow, shape, or other indicium) to a particular toe on that foot.

It is not intended that embodiments of the invention be limited according to the intended procedure the tattoo identifies. Embodiments herein include tattoos indicating non-invasive or invasive procedures including, without limitation, bronchoscopy and bronchoscopic-assisted procedures, gastrointestinal endoscopy and gastrointestinal-endoscopic-assisted procedures, neuro-endoscopic and arthoscopic procedures, placement of catheters for hemodynamic monitoring or therapeutic interventions, cardiovascular procedures, interventional and therapeutic radiological procedures, anesthetic procedures including, without limitation, regional nerve blocks, surgical procedures including, without limitation, intracranial, head and neck extracranial, intrathoracic, intra-abdominal, vascular, cardiac, gastrointestinal, pulmonary, limb, digital, ophthalmic, otolaryngological, rheumatologic, orthopedic, cutaneous, dermatological, breast, pelvic, gynecological, and dental; and procedures performed through a natural body orifice, such as the mouth, nose, vagina, anus or urethra. In such embodiments, the tattoo may be placed at or near the insertion site and should indicate the laterality of the procedure, if relevant.

Additional examples of information that may be provided on the tattoo include the medical practitioner's signature or initials, an insignia, a photo of the body site, and/or an indication of the organ, vessel, joint, or digit number. In some embodiments, the tattoo may provide the date the tattoo was placed on the patient or the date the procedure is to be performed.

The film element of the tattoos used in preferred embodiments of the invention has voids in it, through which the skin is directly exposed. The layout of the film-voids provides information. In exemplary but non-limiting embodiments, one of the film-voids defines an arrow shape. When "filled in" with a skin-bonding, indelible substance expelled from a suitable marking device, another mark inscribed on the skin through another film-void can be identified as either a "left mark" or a "right mark" because the arrow-shaped marked imparts directionality to the surfaces of the film and, thereby, to other marks made through the film. If two film voids are disposed to the right of the arrow such that one is proximate to the head (or "tip") of the arrow, the other to the tail, and marks are made through each, then an "upper right" mark and a "lower right" mark are defined, etc. In effect, the arrow transforms film-voids into a two-dimensional matrix that can convey "matrix-readable" information to the skin. The presence of film-voids is particularly advantageous for entering information that cannot be known in advance. Such information cannot be printed on the tattoo but can be entered succinctly by means of the matrix of film-voids. The matrix itself provides guidance as to where one should inscribe particular bits of information. For example, initials inscribed above the tip of the arrow to the right may be treated, by a predetermined convention, as the patient's initials, while initials inscribed above the tip of the arrow to the left may be treated as the responsible caregiver's initials. Additionally, a film-void may be labeled by means of a printed message disposed in the proximity of the film-void. In some embodiments, the decal may comprise additional film-voids, similarly identified, but providing sites where other pertinent information may be marked. By way of example, without intending any limitation, a film-void may provide a site at which a specifically ordered adjunct to the procedure may be marked on the skin.

Only the practicable size of the decal and of the marking device used to make marks through the film-voids limit the size of the matrix of film-voids. It is to be noted that a "practicable" size for a single cell of the matrix may be in the regime of the wavelength of light if suitable writing and reading devices are employed. However, it may be advantageous in some embodiments to write the matrix-readable information by hand and to read it by eye without need of coding and decoding devices that require elements other than the decal itself and the printed information thereon.

Advantageously, the layout information in the matrix may be retained even after the decal itself has been eradicated by providing a marking device with a suitably indelible ink (see below). In preferred embodiments, the present invention explains and provides instructions for use of the decal, including an explanation that the caregiver's and patient's endorsement on the skin through a suitably pre-determined film-void attests to the correctness of the location of the decal and the correctness of the procedure (including any prohibitions) printed on the decal. These instructions may be printed on backing sheet 20, protective sheet 70 or in other printed instructions provided as a kit, which kit may comprise a selection of pre-printed tattoos, marking pens and other materials, as needed (e.g., an antiseptic "scrub" solution that may be more compatible with the materials that comprise the decal or the marking inks. The instructions may be incorporated into a patient consent form wherein the patient declares an understanding and acknowledgment of the tattoo's conventions for use, etc.

Decals comprising a film-void may be manufactured by methods well-known in the art. Briefly, one surface of water-permeable backing sheet 20 is coated (by spraying or other means) onto that surface a water soluble material which, when dried, forms slip layer 30. When water is later applied to the opposite surface of backing sheet 20 in order to secure the decal onto a skin surface, the water penetrates backing sheet 20 and dissolves slip layer 30. In one method of manufacture, dried slip layer 30 is, in turn, coated with a thin film 40 of material that is water-resistant rather than water-permeable. Water-resistance may be imparted by appropriate selection of the chemical and physical properties of the material and/or by applying the material such that the film it forms is just thick enough to resist penetration of water. A suitable material for the film 40 is commercially available as a standard "offset overprint varnish," but other natural or synthetic materials such as resin solutions having the necessary covering and water-resistant properties may be used and are well-known in the art. Typically, decal films are microscopically thin. Advantageously, the material is compatible with lithographic methods of application, since lithography is a convenient (but non-limiting) way to lay down a film having voids in it. One lithographically prints the film 40 onto the slip layer 30 as a design comprising voids 4, using offset overprint varnish (for example) as the "ink." Other preferred properties of the film include flexibility and resilience so that the applied decal will conform to stretching or other distortion of the skin in regions where the decal is applied.

A design, letters or other symbols may be printed on the dried slip layer 30 or, preferably, on the film layer 40 after it has been laid down on the slip layer 30. The water-resistance of the film 40 serves to keep the printed matter from being dissolved by the water that dissolves the slip layer 30 during application of the decal, and also serves to keep water and wetting agents that may be encountered in the printing process from penetrating the film 40 and dissolving the slip layer 30. It is not intended that embodiments of the invention be limited by the printing method employed. Effective methods include, without limitation, offset methods, flexo printing and gravure printing.

A pressure-sensitive adhesive material is next applied over the printed design in a liquid vehicle that does not dissolve the water-resistant film 40 or the inks used to print information on the film 40. Several vinyl-acrylic copolymers known in the art form aqueous emulsions that can be applied to the film 40 selectively so that no adhesive is deposited in the film-voids 4. Screen (or "silk-screen") printing is a well-known method of application and is advantageous because it deposits a thin, highly uniform and substantially invisible layer which, once dry, does not cause perceptible optical interference between the printed matter on the decal and the skin surface 1 to which it adheres. Finally, a sheet 70 of a material such as a polycarbonate plastic is applied over the adhesive layer 60 to protect against the decal inadvertently sticking to a surface.

The decal may be applied to the skin 1 by removing the protective sheet 70, orienting the printed matter and the film-voids 4 as desired, and pressing the adhesive surface of the decal firmly against a cleaned area of skin 1 to establish initial engagement. Water is then applied to the paper layer 20 such that the water penetrates the paper and softens or dissolves the underlying slip layer 30, leaving behind the film 40 with its design elements 2, printed matter 3 and its film-voids 4 adhered to the skin 1.

Marks may then be made through the film voids 4 to fill in the orienting arrow, to make endorsements, etc. A suitably fine-pointed marker is preferred that expels a marking material indelibly absorbed by the skin. Preferably, the marking material is sufficiently indelible to withstand the process for preparing the skin for surgery with an antiseptic solution such as Betadine® (povidine iodine United States Pharmacopeia 10% w/v) or Hydrex® (pink chlorhexidine gluconate 0.5% w/v in 70% industrial methylated ethanol). As demonstrated by Example 1 herein, the Viomedex® surgical skin-marking pen, felt tipped and charged with permanent ink meets these criteria.

EXPERIMENTAL

Viomedex® and Porex® surgical skin-marking permanent-ink felt-tipped pens and the Sommerlad pen in association with Bonney's Blue ink (BP1980 brilliant green 0.5% w/v, crystal violet 0.5% w/v and alcohol absolute 45% v/v)

Six different surgical marking pens were used to mark a line on the forearm of a volunteer to determine their relative 'permanence' and their ability to withstand surgical skin preparation. Two commonly used alcohol-based skin paints, Betadine® (povidine iodine United States Pharmacopeia 10% w/v) or Hydrex® (pink chlorhexidine gluconate 0.5% w/v in 70% industrial methylated ethanol), were used to clean forearm skin markings made with these six pens. To standardize, a single operator cleaned each marking for a period of 60 seconds. The end results are tabulated in Table 1 as a subjective scoring of durability (0=disappeared, 1=detectable, not legible, 2=barely legible, 3=legible, 4=almost no fading, 5=no discernible fading).

TABLE 1

Pens used and durability score in withstanding surgical skin preparation.

| Pen name | Chlorhexidine gluconate preparation (score 0-5) | Povidone iodine preparation (score 0-5) |
| --- | --- | --- |
| Devon ® skin marker | 1 | 2 |
| Viomedex ® vx 100 | 3 | 3 |
| Porex ® squeeze-mark | 1 | 3 |
| Sharpie ® skin marker | 2 | 2 |
| Securline ® 1000 | 1 | 2 |
| Sommerlad/Bonney's | 1 | 4 |

The results confirm the relative indelibility of the Viomedex® pen in withstanding both alcohol-based skin preparations. The Siommerlad pen with Bonney's blue ink showed superior resilience to povidine iodine but was poor with chlorhexidine gluconate.

The invention claimed is:

1. A temporary tattoo device, comprising:
   a) a film comprising a first surface coated with a skin-adherent adhesive, a second surface disposed opposite said first surface, and a water-resistant material therebetween;
   b) a first film-void that passes through said water-resistant material, said first surface and said second surface;
   c) a first film-void label proximate to said first film-void, wherein said first film-void label comprises a first printed matter label that comprises a first film-void labeling indicia;
   d) a second film-void that passes through said water-resistant material, said first surface and said second surface,
   e) a second film-void label proximate to said second film-void, wherein said second film-void label comprises a second printed matter label that comprises a second film-void labeling indicia.

2. The temporary tattoo device of claim 1, further comprising:
   a) a water-permeable backing sheet disposed along said second surface of said film;
   b) a water-soluble slip-layer disposed between said water-permeable backing sheet and said second surface of said film; and
   c) a removeable protective sheet covering said adhesive-coated first surface of said film.

3. The temporary tattoo device of claim 2, wherein said backing sheet, said slip-layer or said film comprises an antimicrobial substance.

4. The temporary tattoo device of claim 2, wherein said backing sheet is transparent.

5. The temporary tattoo device of claim 2, wherein said protective sheet is transparent.

6. The temporary tattoo device of claim 1, wherein said first film-void labeling indicia identifies a medical procedure.

7. The temporary tattoo device of claim 1, further comprising:
   a third film-void that passes through said water-resistant material, said first surface and said second surface; and
   a third film-void label proximate to said third film-void, wherein said third film-void label comprises a third printed matter label that comprises a third film-void labeling indicia.

8. The temporary tattoo device of claim 1, wherein said second film-void labeling indicia is configured to identify an indelible endorsement mark.

9. A temporary tattoo device kit, comprising:
a) a film, comprising a first surface coated with a skin-adherent adhesive, a second surface disposed opposite said first surface, and a water-resistant material therebetween;
b) a first film-void that passes through said water-resistant material, said first surface and said second surface;
c) a first film-void label proximate to said first film-void, wherein said first film-void label comprises a first printed label that comprises a first film-void labeling indicia; and
d) a second film-void that passes through said water-resistant material, said first surface and said second surface;
e) a second film-void label proximate to said second film void, wherein said second film-void label comprises a second printed matter label that comprises a second film-void labeling indicia.

10. The kit of claim 9, further comprising instructions for use of said temporary tattoo device kit.

11. The kit of claim 10, wherein said instructions are printed on a separate sheet.

12. The kit of claim 10, wherein a patient consent form is incorporated into said instructions.

13. The kit of claim 9, wherein said temporary tattoo device kit further comprises:
a) a water-permeable backing sheet disposed along said second surface of said film;
b) a water-soluble slip-layer disposed between said water-permeable backing sheet and said second surface of said film; and
c) a removeable protective sheet covering said adhesive-coated first surface of said film.

14. The kit of claim 13, further comprising instructions printed on said water-permeable backing sheet.

15. The kit of claim 13, further comprising instructions printed on said removable protective sheet.

16. The kit of claim 9, wherein said kit further comprises a marking pen for indelibly marking skin.

17. The kit of claim 9, wherein said first film-void labeling indicia identifies a medical procedure.

18. The kit of claim 9, wherein said temporary tattoo device kit further comprises a third film-void that passes through said water-resistant material, said first surface and said second surface and a third film void label proximate to said third film void, wherein said third film void label comprises a third printed matter label that comprises a third film-void labeling indicia.

19. The kit of claim 9, wherein said second film-void labeling indicia is configured to identify an indelible endorsement mark.

* * * * *